(12) United States Patent
Olson et al.

(10) Patent No.: US 7,553,967 B2
(45) Date of Patent: Jun. 30, 2009

(54) 1,2-DIHYDROQUINOLINE DERIVATIVES AND METHOD FOR USING THE SAME TO TREAT HIV INFECTIONS

(75) Inventors: Matthew Olson, Bardonia, NY (US); Martin Di Grandi, Harriman, NY (US); Amarnauth Prashad, New City, NY (US)

(73) Assignee: Wyeth, Madison, NJ (US)

( * ) Notice: Subject to any disclaimer, the term of this patent is extended or adjusted under 35 U.S.C. 154(b) by 485 days.

(21) Appl. No.: 11/076,936

(22) Filed: Mar. 11, 2005

(65) Prior Publication Data

US 2005/0203129 A1 Sep. 15, 2005

Related U.S. Application Data

(60) Provisional application No. 60/552,809, filed on Mar. 12, 2004.

(51) Int. Cl.
C07D 215/38 (2006.01)
(52) U.S. Cl. .................. 546/159; 546/153; 546/156
(58) Field of Classification Search ............ 546/153, 546/156, 159
See application file for complete search history.

(56) References Cited

U.S. PATENT DOCUMENTS

| | | | | |
|---|---|---|---|---|
| 4,792,611 | A | 12/1988 | Donovan | 548/542 |
| 4,968,680 | A | 11/1990 | Mochida et al. | 514/243 |
| 5,223,490 | A | 6/1993 | Babiak et al. | 514/311 |
| 5,514,690 | A | 5/1996 | Atwal et al. | 514/311 |
| 5,641,785 | A * | 6/1997 | Jegham et al. | 514/291 |
| 5,939,435 | A | 8/1999 | Babiak et al. | 514/311 |
| 6,093,821 | A | 7/2000 | Jones et al. | 544/333 |
| 6,388,081 | B1 | 5/2002 | Hayes et al. | 546/165 |
| 6,511,966 | B2 | 1/2003 | Ghosh et al. | 514/31 |
| 6,930,104 | B2 * | 8/2005 | Kakihana et al. | 514/217 |
| 2003/0162777 | A1 * | 8/2003 | Leonardi et al. | 514/228.2 |
| 2003/0181446 | A1 * | 9/2003 | Leonardi et al. | 514/228.2 |

FOREIGN PATENT DOCUMENTS

| | | |
|---|---|---|
| EP | 0 023 306 | 7/1980 |
| EP | 0579469 | 1/1994 |
| EP | 1382598 | 1/2004 |
| WO | WO 92/16508 | 10/1992 |
| WO | WO 2004/059012 | 7/2004 |

OTHER PUBLICATIONS

Parker, Organic Letters, vol. 4(24), pp. 4265-4268, 2002.*
Evain, CA 138:98395, abstract only of Acta Crystallographic, E58(10), pp. o1121-o1122, 2002.*
Takamura, J of American Chemical Society, vol. 123(28), pp. 6801-6808, 2001.*
Takamura, J American Chemical Society, 122(26), p. 6327-6328, 2000.*
Telesnitsky, Blain and Goff, Methods in Enzymology, vol. 262, pp. 347-362, 1995.
Goff, Traktman and Baltimore, J. Virology, vol. 38 (I), pp. 239-248, 1981.
Font et al., "Synthesis And Evaluation of New Reissert Analogs As HIV-1 Reverse Transcriptase Inhibitors . . . ", Drug Design and Discovery, vol. 14 (4), 1997, pp. 305-332.
Hiessbaeck et al., "Synthesis And In Vitro Multidrug Resistance Modulating Activity . . . ", J. Med. Chem., vol. 42, 1999, pp. 1921-1926.
Donnelly and Farrell, "The Chemistry of 2-Amino Analogues of 2'-Hydroxychalcone And Its Derivatives", J. Org. Chem., vol. 55 (6), 1990, pp. 1757-1761.
Database Beilstein 1988, database accession No. 1246949 (BRN).
Database Beilstein 1988, database accession No. 2575354 (CNR).
Database Beilstein 1988, database accession No. 3135790 (CNR).
Database Beilstein 1988, database accession No. 2622417 (CNR).

* cited by examiner

*Primary Examiner*—D. Margaret Seaman
(74) *Attorney, Agent, or Firm*—Fitzpatrick, Cella, Harper & Scinto

(57) ABSTRACT

The present invention is directed to compound of formula (A):

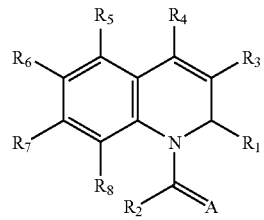

wherein $R_1$ is selected from (a) alkyl, alkenyl, alkynyl, cycloalkyl, aryl, and heteroaryl, or (b) CN and —C($NR_{10}R_{11}$)=N—$R_{12}$, $R_2$ is selected from the group consisting of alkyl, alkenyl, alkynyl, cycloalkyl, aryl and heteroaryl, $R_3$-$R_{12}$ are as described within the specification, and A is O, $NR_9$ or S, or a prodrug, a pharmaceutically acceptable salt or a pharmaceutically active metabolite thereof, provided that $R_1$ is not alkyl when $R_2$ is pyridine, provided that at least one of $R_3$-$R_8$ is not H or F when A is O, $R_1$ is (b) and $R_2$ is a phenyl ring, a phenyl ring substituted at the para position with halo, —CN, —$OCH_3$, —$CF_3$ or —$CO_2CH_3$, a quinoline or an ethylene substituted with a phenyl ring or a 3,4-methylenedioxyphenyl moiety, provided that $R_4$ is not methyl when $R_3$ and $R_5$-$R_8$ are H, A is O, $R_1$ is (b) and $R_2$ is 4-chlorophenyl, and provided that $R_6$ is not Cl when $R_3$-$R_5$ and $R_7$-$R_8$ are H, $R_1$ is CN and $R_2$ is phenyl. This invention is also directed to methods of using the same for treating HIV infections, or AIDS, or preventing replication.

12 Claims, No Drawings

1,2-DIHYDROQUINOLINE DERIVATIVES AND METHOD FOR USING THE SAME TO TREAT HIV INFECTIONS

This application claims the benefit of U.S. Provisional Application No. 60/552,809, filed on Mar. 12, 2004.

BACKGROUND OF THE INVENTION

1. Field of the Invention

This invention relates to 1,2-dihydroquinoline derivatives and methods for their use in treating HIV infections. These compounds are useful for treating retrovirus-associated cancer, and modulating reverse transcriptase, RNase, HIV polymerase.

2. Related Background Art

The retrovirus designated human immunodeficiency virus (HIV) is the etiological agent of the complex disease that includes progressive destruction of the immune system and degeneration of the central and peripheral nervous system (acquired immune deficiency syndrome; AIDS). A common feature of retrovirus replication is reverse transcription of the RNA genome by a virally encoded reverse transcriptase. Reverse transcriptase is implicated in the infectious lifecycle of HIV, and compounds such as nucleoside and non-nucleoside reverse transcriptase inhibitors, which interfere with the function of this enzyme, have shown utility in the treatment of conditions including AIDS.

Presently, there are four categories of drugs used to treat HIV infection, which include nucleoside analogue reverse transcriptase inhibitors, non-nucleoside reverse transcriptase inhibitors and protease inhibitors. Reverse transcriptase inhibitors, including the nucleoside and non-nucleoside categories, interfere with HIV reverse transcriptase, which, as noted above, is required for viral replication. Protease inhibitors interfere with the enzyme protease, which plays a major role in viral infection. Forms of anti-HIV therapy include giving only one reverse transcriptase inhibitor at a time (monotherapy), a combination of two or more reverse transcriptase inhibitors (combination therapy), and a combination of reverse transcriptase inhibitors and protease inhibitors (combination therapy with protease inhibitors). Nucleoside analogues include AZT (zidovudine, Retrovir), ddI (didanosine, Videx), 3TC (lamivudine, Epivir), d4T (stavudine, Zerit), abacavir (Ziagen) and ddC (zalcitabine, Hivid). AZT and 3TC are also available in a single combined pill called Combivir and AZT, 3TC and abacavir are available in a single combined pill called Trizivir. Tenofovir (Viread), a nucleotide analogue, is the only nucleotide analogue currently available for prescription and is only licensed to give people on their second or later treatment combination, although it may be given to people in their first-line treatment. Nucleotide analogues are very similar to nucleoside analogues. The only difference is that nucleotide analogues, unlike nucleoside analogues, are chemically preactivated and thus require less processing in the body for them to become active. Non-nucleoside reverse transcriptase inhibitors include Sustiva, nevirapine (Viramune), and delavirdine (Rescriptor).

Many of the treatments which inhibit reverse transcriptase activity that are currently available, particularly the nucleoside analogues, are associated with serious side effects and require long term treatment to be effective. In addition, the virus is able to mutate in response to the drugs and becomes resistant to them. Therefore, there is a constant need to provide new and better treatments for HIV and AIDS and particularly new drugs that inhibit HIV reverse transcriptase.

Derivatives of 1,2-dihydroquinoline are known to possess activity which make them useful as herbicides and therapeutic agents.

1,2-Dihydroquinoline derivatives are disclosed in European Patent Application No. 0 579 469 for use as herbicides with selectivity between crops and weeds.

The following U.S. patents disclose 1,2-dihydroquinoline derivatives which have activity that may be useful in the treatment of various diseases. U.S. Pat. No. 4,968,680 discloses compounds that are potent diuretic agents that may be useful in the treatment of hypertension, edema, and removing ascites. Potassium channel activating compounds for use as antiischemic agents were described in U.S. Pat. No. 5,514,690. In U.S. Pat. No. 6,511,966, 1,2-dihydroquinoline compounds that are mitochondria protecting agents were disclosed. These compounds are useful for treating diseases in which mitochondrial dysfunction leads to tissue degeneration, such as Alzheimer's disease, diabetes mellitus and Parkinson's disease. Compounds capable of increasing HDL-C concentrations for the treatment of dyslipoproteinanians and coronary heart disease were disclosed in U.S. Pat. No. 5,939,435. 1,2-Dihydroquinoline compounds described in U.S. Pat. No. 6,093,821 are modulators of steroid receptors.

The International Publication No. WO 92/16508 discloses 1,2-dihydroquinoline compounds that are useful for the treatment of AIDs and related complexes, but these compounds differ in structure from those of the present invention.

U.S. Pat. No. 6,388,081 discloses combination libraries containing two or more 1,2-dihydroquinoline derivatives and methods of generating such libraries.

BRIEF SUMMARY OF THE INVENTION

The present invention is directed to compounds of formula (A):

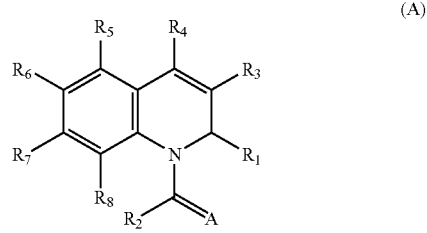

wherein:

$R_1$ is selected from (a) alkyl, alkenyl, alkynyl, cycloalkyl, aryl, and heteroaryl or (b) CN and —C($NR_{10}R_{11}$)=N—$R_{12}$, any of which may be optionally substituted;

$R_2$ is selected from alkyl, alkenyl, alkynyl, cycloalkyl, aryl and heteroaryl, any of which may be optionally substituted;

$R_3$-$R_8$ are independently selected from H, halo, hydroxy, alkyl, haloalkyl, acyl, aryl, heteroaryl, cycloalkyl, heterocycloalkyl, arylalkyl, heteroarylalkyl, CN, amino, alkylamino, dialkylamino, nitro, —COOH, —C(O)-alkyl, —C(O)-aryl, alkoxy, haloalkoxy, mercapto, alkylthio, arylthio, amido, sulfamido, sulfonylalkyl, alkylamido, dialkylamido, —$SO_2$NH-alkyl, —$SO_2$N-(alkyl)$_2$ and —$SO_3$H, any of which may be optionally substituted;

A is O, $NR_9$ or S;

$R_{10}$ and $R_{11}$ are independently selected from H, alkyl, aryl, arylalkyl, heteroaryl, heteroarylalkyl, cycloalkyl, cycloalkylalkyl, heterocycloalkyl and heterocycloalkylalkyl, any of which may be optional substituted; and $R_9$ and $R_{12}$ are selected from alkoxy, —OC(O)-alkyl, —OC(O)-aryl, cycloalkyl, aryl, heterocycloalkyl, heteroaryl and hydroxy, any of which may be optionally substituted; and or a prodrug, a pharmaceutically acceptable salt or a pharmaceutically active metabolite thereof;

provided that at least one of $R_3$-$R_8$ is not H or F when A is O, $R_1$ is (b) and $R_2$ is a phenyl ring, a phenyl ring substituted at the para position with halo, —CN, —OCH$_3$, —CF$_3$ or —CO$_2$CH$_3$, a quinoline or an ethylene substituted with a phenyl ring or a 3,4-methylenedioxyphenyl moiety;

provided that $R_4$ is not methyl when $R_3$ and $R_5$-$R_8$ are H, A is O, $R_1$ is (b) and $R_2$ is 4-chlorophenyl; and provided that $R_6$ is not Cl when $R_3$-$R_5$ and $R_7$-$R_8$ are H, $R_1$ is CN and $R_2$ is phenyl.

provided that $R_1$ is not alkyl when $R_2$ is pyridine.

The present invention is further directed to compounds of formula (I):

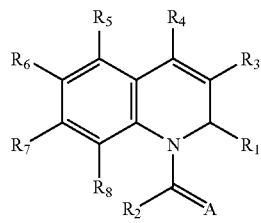

(I)

wherein:

$R_1$ is selected from alkyl, alkenyl, alkynyl, cycloalkyl, aryl, and heteroaryl, any of which may be optionally substituted;

$R_2$ is selected from alkyl, alkenyl, alkynyl, cycloalkyl, aryl and heteroaryl, any of which may be optionally substituted;

$R_3$-$R_8$ are independently selected from H, halo, hydroxy, alkyl, haloalkyl, acyl, aryl, heteroaryl, cycloalkyl, heterocycloalkyl, arylalkyl, heteroarylalkyl, CN, amino, alkylamino, dialkylamino, nitro, —COOH, —C(O)-alkyl, —C(O)-aryl, alkoxy, haloalkoxy, mercapto, alkylthio, arylthio, amido, sulfamido, sulfonylalkyl, alkylamido, dialkylamido, —SO$_2$NH-alkyl, —SO$_2$N-(alkyl)$_2$ and —SO$_3$H, any of which may be optionally substituted;

A is O, NR$_9$ or S;

$R_9$ is selected from alkoxy, —OC(O)-alkyl, —OC(O)-aryl, cycloalkyl, aryl, heterocycloalkyl, heteroaryl and hydroxy, any of which may be optionally substituted; and or a prodrug, a pharmaceutically acceptable salt or a pharmaceutically active metabolite thereof;

provided that $R_1$ is not alkyl when $R_2$ is pyridine.

The present invention is additionally directed to compounds of formula (II):

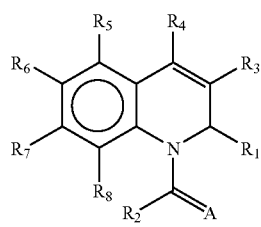

(II)

wherein:

$R_1$ is CN or —C(NR$_{10}$R$_{11}$)=N—R$_{12}$;

$R_2$ is selected from alkyl, alkenyl, alkynyl, cycloalkyl, aryl and heteroaryl, any of which may be optionally substituted;

$R_3$-$R_8$ are independently selected from H, halo, hydroxy, alkyl, haloalkyl, acyl, aryl, heteroaryl, cycloalkyl, heterocycloalkyl, arylalkyl, heteroarylalkyl, CN, amino, alkylamino, dialkylamino, nitro, —COOH, —C(O)-alkyl, —C(O)-aryl, alkoxy, haloalkoxy, mercapto, alkylthio, arylthio, amido, sulfamido, sulfonylalkyl, alkylamido, dialkylamido, —SO$_2$NH-alkyl, —SO$_2$N-(alkyl)$_2$ and —SO$_3$H, any of which may be optionally substituted;

A is O, NR$_9$ or S;

$R_{10}$ and $R_{11}$ are independently selected from H, alkyl, aryl, arylalkyl, heteroaryl, heteroarylalkyl, cycloalkyl, cycloalkylalkyl, heterocycloalkyl and heterocycloalkylalkyl, any of which may be optional substituted; and $R_9$ and $R_{12}$ are independently selected from alkoxy, —OC(O)-alkyl, —OC(O)-aryl, cycloalkyl, aryl, heterocycloalkyl, heteroaryl and hydroxy, any of which may be optionally substituted;

or a prodrug, a pharmaceutically acceptable salt or a pharmaceutically active metabolite thereof;

provided that at least one of $R_3$-$R_8$ is not H or F when A is O and $R_2$ is a phenyl ring, a phenyl ring substituted at the para position with halo, —CN, —OCH$_3$, —CF$_3$ or —CO$_2$CH$_3$, a quinoline or an ethylene substituted with a phenyl ring or a 3,4-methylenedioxyphenyl moiety;

provided that $R_4$ is not methyl when $R_3$ and $R_5$-$R_8$ are H, A is O and $R_2$ is 4-chlorophenyl; and provided that $R_6$ is not Cl when $R_3$-$R_5$ and $R_7$-$R_8$ are H, $R_1$ is CN and $R_2$ is phenyl.

The compounds of this invention are useful for inhibiting reverse transcriptase activity, polymerase activity, and RNase H activity, and more particularly, inhibiting the RNase H activity and RNA dependent DNA polymerase (RDDP) activity of HIV reverse transcriptase, and its resistant varieties, and are modulators, especially inhibitors thereof, for the treatment and prevention of HIV and AIDS. The 1,2-dihydroquinoline derivatives of the present invention are also useful for treating retrovirus-associated cancer, such as adenocarcinoma of the breast.

This invention is also directed to a method of inhibiting HIV infections comprising the step of administering to a mammal in need thereof an effective amount of a compound of formula (A):

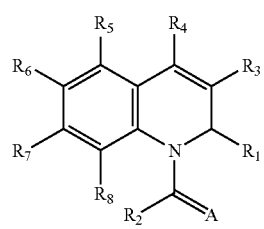

(A)

wherein:

$R_1$ is selected from (a) alkyl, alkenyl, alkynyl, cycloalkyl, aryl, and heteroaryl or (b) CN and —C(NR$_{10}$R$_{11}$)=N—R$_{12}$, any of which may be optionally substituted;

$R_2$ is selected from the group consisting of alkyl, alkenyl, alkynyl, cycloalkyl, aryl and heteroaryl, any of which may be optionally substituted;

$R_3$-$R_8$ are independently selected from the group consisting of H, halo, hydroxy, alkyl, haloalkyl, acyl, aryl, heteroaryl, cycloalkyl, heterocycloalkyl, arylalkyl, heteroarylalkyl, CN, amino, alkylamino, dialkylamino, nitro, —$CO_2H$, —C(O)-alkyl, —C(O)-aryl, alkoxy, haloalkoxy, mercapto, alkylthio, arylthio, amido, —$SO_2NH$, —$SO_3H$, —$SO_2NH$-alkyl, —$SO_2N$-(aklyl)$_2$, aryloxy and heteroaryloxy, any of which may be optionally substituted;

$R_{10}$ and $R_{11}$ are independently selected from the group consisting of H, alkyl, aryl, arylalkyl, heteroaryl, heteroarylalkyl, cycloalkyl, cycloalkylalkyl, heterocycloalkyl and heterocycloalkylalkyl, any of which may be optionally substituted;

$R_9$ and $R_{12}$ are independently selected from the group consisting alkoxy, —OC(O)-alkyl, —OC(O)-aryl, cycloalkyl, aryl, heterocycloalkyl, heteroaryl and hydroxy, any of which may be optionally substituted; and A is O, $NR_9$ or S;

or a prodrug, a pharmaceutically acceptable salt or a pharmaceutically active metabolite thereof;

provided that at least one of $R_3$-$R_8$ is not H or F when A is O, $R_1$ is (b) and $R_2$ is a phenyl ring, a phenyl ring substituted at the para position with halo, —CN, —$OCH_3$, —$CF_3$ or —$CO_2CH_3$, a quinoline or an ethylene substituted with a phenyl ring or a 3,4-methylenedioxyphenyl moiety; and provided that $R_4$ is not methyl when $R_3$ and $R_5$-$R_8$ are H, A is O, $R_1$ is (b) and $R_2$ is 4-chlorophenyl.

Another aspect of this invention is a method for inhibiting HIV infections comprising contacting RNase with a compound of formula (A):

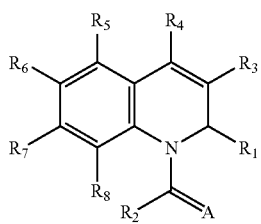

(A)

wherein:

$R_1$ is selected from the group consisting of (a) alkyl, alkenyl, alkynyl, cycloalkyl, aryl, and heteroaryl or (b) CN and —C($NR_{10}R_{11}$)=N—$R_{12}$, any of which may be optionally substituted;

$R_2$ is selected from the group consisting of alkyl, alkenyl, alkynyl, cycloalkyl, aryl and heteroaryl, any of which may be optionally substituted;

$R_3$-$R_8$ are independently selected from the group consisting of H, halo, hydroxy, alkyl, haloalkyl, acyl, aryl, heteroaryl, cycloalkyl, heterocycloalkyl, arylalkyl, heteroarylalkyl, CN, amino, alkylamino, dialkylamino, nitro, —$CO_2H$, —C(O)-alkyl, —C(O)-aryl, alkoxy, haloalkoxy, mercapto, alkylthio, arylthio, amido, —$SO_2NH$, —$SO_3H$, —$SO_2NH$-alkyl, —$SO_2N$-(aklyl)$_2$, aryloxy and heteroaryloxy, any of which may be optionally substituted;

$R_{10}$ and $R_{11}$ are independently selected from the group consisting of H, alkyl, aryl, arylalkyl, heteroaryl, heteroarylalkyl, cycloalkyl, cycloalkylalkyl, heterocycloalkyl and heterocycloalkylalkyl, any of which may be optionally substituted;

$R_9$ and $R_{12}$ are independently selected from the group consisting alkoxy, —OC(O)-alkyl, —OC(O)-aryl, cycloalkyl, aryl, heterocycloalkyl, heteroaryl and hydroxy, any of which may be optionally substituted; and A is O, $NR_9$ or S;

or a prodrug, a pharmaceutically acceptable salt or a pharmaceutically active metabolite thereof, provided that at least one of $R_3$-$R_8$ is not H or F when A is O, $R_1$ is (b) and $R_2$ is a phenyl ring, a phenyl ring substituted at the para position with halo, —CN, —$OCH_3$, —$CF_3$ or —$CO_2CH_3$, a quinoline or an ethylene substituted with a phenyl ring or a 3,4-methylenedioxyphenyl moiety; and provided that $R_4$ is not methyl when $R_3$ and $R_5$-$R_8$ are H, A is O, $R_1$ is (b) and $R_2$ is 4-chlorophenyl.

Another aspect of this invention is a method for inhibiting HIV infections comprising contacting polymerase with a compound of formula (A):

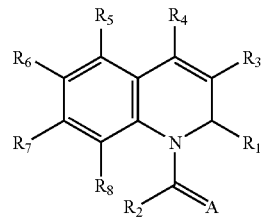

(A)

wherein:

$R_1$ is selected from the group consisting of (a) alkyl, alkenyl, alkynyl, cycloalkyl, aryl, and heteroaryl or (b) CN and —C($NR_{10}R_{11}$)=N—$R_{12}$, any of which may be optionally substituted;

$R_2$ is selected from the group consisting of alkyl, alkenyl, alkynyl, cycloalkyl, aryl and heteroaryl, any of which may be optionally substituted;

$R_3$-$R_8$ are independently selected from the group consisting of H, halo, hydroxy, alkyl, haloalkyl, acyl, aryl, heteroaryl, cycloalkyl, heterocycloalkyl, arylalkyl, heteroarylalkyl, CN, amino, alkylamino, dialkylamino, nitro, —$CO_2H$, —C(O)-alkyl, —C(O)-aryl, alkoxy, haloalkoxy, mercapto, alkylthio, arylthio, amido, —$SO_2NH$, —$SO_3H$, —$SO_2NH$-alkyl, —$SO_2N$-(aklyl)$_2$, aryloxy and heteroaryloxy, any of which may be optionally substituted;

$R_{10}$ and $R_{11}$ are independently selected from the group consisting of H, alkyl, aryl, arylalkyl, heteroaryl, heteroarylalkyl, cycloalkyl, cycloalkylalkyl, heterocycloalkyl and heterocycloalkylalkyl, any of which may be optionally substituted;

$R_9$ and $R_{12}$ are independently selected from the group consisting alkoxy, —OC(O)-alkyl, —OC(O)-aryl, cycloalkyl, aryl, heterocycloalkyl, heteroaryl and hydroxy, any of which may be optionally substituted; and A is O, $NR_9$ or S;

or a prodrug, a pharmaceutically acceptable salt or a pharmaceutically active metabolite thereof, provided that at least one of $R_3$-$R_8$ is not H or F when A is O, $R_1$ is (b) and $R_2$ is a phenyl ring, a phenyl ring substituted at the para position with halo, —CN, —$OCH_3$, —$CF_3$ or —$CO_2CH_3$, a quinoline or an ethylene substituted with a phenyl ring or a 3,4-methylenedioxyphenyl moiety; and provided that $R_4$ is not methyl when $R_3$ and $R_5$-$R_8$ are H, A is O, $R_1$ is (b) and $R_2$ is 4-chlorophenyl.

For purposes of this invention the term "alkyl" includes either straight or branched alkyl moieties. The length of a straight alkyl moiety can be from 1 to 12 carbon atoms, but is preferably 1 to 8 carbon atoms. Branched alkyl moieties can contain 3 to 12 carbon atoms, but preferably contain 3 to 8 carbon. These alkyl moieties may be unsubstituted or substituted. The term "alkenyl" refers to a substituted or unsubstituted radical aliphatic hydrocarbon containing one double bond and includes alkenyl moieties of both straight, preferably of 2 to 8 carbon atoms and branched, preferably of 3 to 8 carbon atoms. Such alkenyl moieties may exist in the E or Z configurations; the compounds of this invention include both configurations. The term "alkynyl" includes substituted and unsubstituted alkynyl moieties of both straight chain containing 2 to 8 carbon atoms and branched containing 4 to 8 carbon atoms having at least one triple bond. The term "cycloalkyl" refers to substituted or unsubstituted alicyclic hydrocarbon groups having 3 to 12 carbon atoms and includes but is not limited to: cyclopropyl, cyclobutyl, cyclopentyl, cyclohexyl, cycloheptyl, norbornyl, or adamantyl. For purposes of this invention the term "aryl" is defined as an aromatic hydrocarbon moiety and may be substituted or unsubstituted and preferably having 6 to 12 carbon atoms. An aryl may be selected from but not limited to, the group consisting of: phenyl, α-naphthyl, β-naphthyl, biphenyl, anthryl, tetrahydronaphthyl, phenanthryl, fluorenyl, indanyl, biphenylenyl, acenaphthenyl, acenaphthylenyl, or phenanthrenyl groups.

For purposes of this invention the term "heteroaryl" is defined as an aromatic heterocyclic ring system (monocyclic or bicyclic) and may be substituted or unsubstituted where the heteroaryl moieties are five or six membered rings containing 1 to 4 heteroatoms selected from the group consisting of S, N, and O, and include but are not limited to: (1) furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, pyrrolidinyl; (2) a bicyclic aromatic heterocycle where a phenyl, pyridine, pyrimidine or pyridizine ring is: (i) fused to a 6-membered aromatic (unsaturated) heterocyclic ring having one nitrogen atom; (ii) fused to a 5 or 6-membered aromatic (unsaturated) heterocyclic ring having two nitrogen atoms; (iii) fused to a 5-membered aromatic (unsaturated) heterocyclic ring having one nitrogen atom together with either one oxygen or one sulfur atom; or (iv) fused to a 5-membered aromatic (unsaturated) heterocyclic ring having one heteroatom selected from O, N or S. Preferably a heterocycle moiety contains 2 to 9 carbon atoms.

For purposes of this invention the term "heterocycloalkyl" refers to a substituted or unsubstituted alicyclic ring system (moncyclic or bicyclic) wherein the heterocycloalkyl moieties are 3 to 12 membered rings containing 1 to 6 heteroatoms selected from the group consisting of S, N, and O. Preferably a heterocycloalkyl contains 2 to 11 carbon atoms.

For the purposes of this invention the term "alkoxy" is defined as $C_1$-$C_{12}$alkyl-O—; the term "aryloxy" is defined as aryl-O—; the term "heteroaryloxy" is defined as heteroaryl-O—; the term "cycloalkyloxy" is defined as cycloalkyl-O—; the term "heterocycloalkyloxy" is defined as heterocycloalkyl-O—; wherein alkyl, aryl, heteroaryl, cycloalkyl, and heterocycloalkyl are as defined above.

For purposes of this invention the term "arylalkyl" is defined as aryl-$C_1$-$C_8$-alkyl, preferably the arylalkyl moiety is comprised of 7-12 carbon atoms. Arylalkyl moieties include benzyl, 1-phenylethyl, 2-phenylethyl, 3-phenylpropyl, 2-phenylpropyl and the like.

For purposes of this invention the term "heteroarylalkyl" is defined as heteroaryl-$C_1$-$C_8$-alkyl, preferably the heteroarylalkyl moiety is comprised of 3-17 carbon atoms.

For purposes of this invention the term "alkylaryl" is defined as $C_1$-$C_8$-alkyl-aryl. Preferably the alkylaryl moiety is comprised of 7-12 carbon atoms.

For purposes of this invention the term "alkylthio" is defined as $C_1$-$C_8$-alkyl-S—.

For purposes of this invention "alkoxyalkyl," "cycloalkylalkyl," and "heterocycloalkyl-alkyl" denote an alkyl group as defined above that is further substituted with an alkoxy, cycloalkyl, or heterocycloalkyl group as defined above.

For purposes of this invention "alkoxyalkoxy" denote an alkoxy group as defined above that is further substituted with an alkoxy group as defined above.

For purposes of this invention "arylthio" and "heteroarylthio" denote a thio group that is further substituted with an aryl or heteroaryl group as defined above.

The terms "monoalkylamino" and "dialkylamino" refer to moieties with one or two alkyl groups wherein the alkyl chain is 1 to 8 carbons and the groups may be the same or different. The terms monoalkylaminoalkyl and dialkylaminoalkyl refer to monoalkylamino and dialkylamino moieties with one or two alkyl groups (the same or different) bonded to the nitrogen atom which is attached to an alkyl group of 1 to 8 carbon atoms.

"Acyl" is a radical of the formula —(C=O)-alkyl or —(C=O)-perfluoroalkyl wherein the alkyl radical or perfluoroalkyl radical is 1 to 8 carbon atoms; preferred examples include but are not limited to, acetyl, propionyl, butyryl, trifluoroacetyl.

The term "carbonyl" or "oxo" refers to the radical —C(O)—.

Saturated or partially saturated heteroaryl groups are defined in this invention as heterocyclic rings selected from but not limited to the moieties: azetidinyl, 1,4-dioxanyl, hexahydroazepinyl, piperazinyl, piperidinyl, pyrrolidinyl, morpholinyl, thiomorpholinyl, dihydrobenzimidazolyl, dihydrobenzofuranyl, dihydrobenzothienyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, dihydro-1,4-dioxanyl, tetrahydrofuranyl, tetrahydrothienyl, tetrahydroquinolinyl, and tetrahydroisoquinolinyl.

The term "substituent" is used herein to refer to an atom radical, a functional group radical or a moiety radical that replaces a hydrogen radical on a molecule. Unless expressly stated otherwise, it should be assumed that any of the substituents may be optionally substituted with one or more groups selected from: alkyl, halogen, haloalkyl, hydroxyalkyl, nitro, amino, hydroxy, cyano, alkylamino, dialkylamino, alkoxy, haloalkoxy, alkoxyalkyl, alkoxyalkoxy, oxo, alkylthio, mercapto, haloalkylthio, aryl, aryloxy, arylthio, heteroaryl, heteroaryloxy, heteroarylthio, acyl, —$CO_2$-alkyl, —$SO_3H$, —$SO_2NH_2$, —$SO_2NH$-alkyl, —$SO_2NH$-(alkyl)$_2$, —$CO_2H$, —$CO_2NH_2$, —$CO_2NH$-alkyl and —$CO_2N$-(alkyl)$_2$.

For the purposes of this invention the term "substituted" refers to where a hydrogen radical on a molecule has been replaced by another atom radical, a functional group radical or a moiety radical; these radicals being generally referred to as "substituents."

In one embodiment the substituted aryl, heteroaryl, cycloalkyl, or heterocycloalkyl, may be optionally mono-, di-, tri- or tetra-substituted with substituents selected from, but not limited to, the group consisting of alkyl, acyl, alkoxy, alkoxyalkyl, alkoxyalkoxy, cyano, halogen, hydroxy, nitro, trifluoromethyl, trifluoromethoxy, trifluoropropyl, amino, alkylamino, dialkylamino, dialkylaminoalkyl, hydroxyalkyl, alkylthio, —$SO_3H$, —$SO_2NH_2$, —$SO_2NHalkyl$, —$SO_2N(alkyl)_2$, —$CO_2H$, —$CO_2$— alkyl, $CO_2NH_2$, $CO_2NHalkyl$, and —$CO_2N(alkyl)_2$. Preferred substituents for aryl, heteroaryl, cycloalkyl, or heterocycloalkyl, include but are not limited to: alkyl, halogen, amino, alkylamino, dialkylamino, trifluoromethyl, trifluoromethoxy, arylalkyl, and alkylaryl.

A preferred embodiment of this invention is where the compounds of formula (I) are defined by:

$R_1$ is selected from the group consisting of $C_1$-$C_8$ alkyl, $C_2$-$C_8$ alkenyl, $C_3$-$C_8$ alkynyl, $C_3$-$C_{12}$ cycloalkyl, $C_6$-$C_{12}$ aryl, and $C_2$-$C_9$ heteroaryl any of which may be optionally substituted;

$R_2$ is selected from the group consisting of $C_1$-$C_8$ alkyl, $C_1$-$C_8$ alkenyl, $C_1$-$C_8$ alkynyl, $C_3$-$C_{12}$ cycloalkyl, $C_6$-$C_{12}$ aryl and $C_2$-$C_9$ heteroaryl, any of which may be optionally substituted;

$R_3$-$R_8$ are independently selected from the group consisting of H, halo, hydroxy, $C_1$-$C_8$ alkyl, $C_1$-$C_8$ haloalkyl, acyl, $C_2$-$C_9$ heteroaryl, $C_6$-$C_{12}$ aryl, $C_3$-$C_{12}$ cycloalkyl, $C_2$-$C_{11}$ heterocycloalkyl, $C_7$-$C_{12}$ arylalkyl, $C_6$-$C_{11}$ heteroarylalkyl, CN, amino, $C_1$-$C_8$ alkylamino, $C_1$-$C_8$ dialkylamino, Nitro, —COOH, —C(O)—$C_1$-$C_8$ alkyl, C(O)$C_6$-$C_{12}$-aryl, $C_1$-$C_8$ alkoxy, $C_1$-$C_8$ haloalkoxy, mercapto, $C_1$-$C_8$ alkylthio, $C_6$-$C_{12}$ arylthio, amido, sulfamido, —$SO_2$—$C_1$-$C_8$ alkyl, $C_1$-$C_8$ alkylamido, $C_1$-$C_8$ dialkylamido, —$SO_2NH$—C—$C_8$ alkyl, —$SO_2$—$N(C_1$-$C_8$ alkyl$)_2$ and —$SO_3H$, any of which may be optional substituted; and $R_9$ is selected from the group consisting of H, $C_1$-$C_8$ alkyl, $C_2$-$C_8$ alkenyl, $C_2$-$C_8$ alkynyl, $C_1$-$C_8$ alkoxy, —OC(O)—$C_1$-$C_8$ alkyl, —OC(O)—$C_6$-$C_{12}$ aryl, $C_3$-$C_{12}$ cycloalkyl, $C_6$-$C_{12}$ aryl, $C_2$-$C_{11}$ heterocycloalkyl, $C_2$-$C_9$ heteroaryl and hydroxy, any of which may be optionally substituted;

or a prodrug, a pharmaceutically acceptable salt, or a pharmaceutically active metabolite.

A more specific embodiment of the compounds of formula (I) is where $R_1$ is optionally substituted alkenyl, $R_2$ is aryl or heteroaryl, and preferably optionally substituted phenyl, $R_3$-$R_8$ are independently selected from H, alkyl, haloalkyl, halo, alkoxy, hydroxy, CN, amino, alkylamino, dialkylamino, alkylthio or —$SO_2NH_2$, and A is O, or a prodrug, a pharmaceutically acceptable salt or a pharmaceutically active metabolite thereof.

A preferred embodiment of this invention is where the compounds of formula (II) are defined by:

$R_2$ being selected from the group consisting of $C_1$-$C_8$ alkyl, $C_2$-$C_8$ alkenyl, $C_2$-$C_8$ alkynyl, $C_3$-$C_{12}$ cycloalkyl, $C_6$-$C_{12}$ aryl and $C_2$-$C_9$ heteroaryl, any of which may be optionally substituted;

$R_3$-$R_8$ are independently selected from the group consisting of H, halo, hydroxy, $C_1$-$C_8$ alkyl, $C_1$-$C_8$ haloalkyl, acyl, $C_2$-$C_9$ heteroaryl, $C_6$-$C_{12}$ aryl, $C_3$-$C_{12}$ cycloalkyl, $C_2$-$C_{11}$ heterocycloalkyl, $C_7$-$C_{12}$ arylalkyl, $C_3$-$C_{17}$ heteroaryl-alkyl, CN, amino, $C_1$-$C_8$ alkylamino, $C_1$-$C_8$ dialkylamino, Nitro, —COOH, —C(O)—$C_1$-$C_8$ alkyl, —C(O)—$C_6$-$C_{12}$-aryl, $C_1$-$C_8$ alkoxy, $C_1$-$C_8$ haloalkoxy, mercapto, $C_1$-$C_8$ alkylthio, $C_6$-$C_{12}$ arylthio, amido, sulfamido, —$SO_2$—$C_1$-$C_8$ alkyl, $C_1$-$C_8$ alkylamido, $C_1$-$C_8$ dialkylamido, —$SO_2NH$—$C_{1-8}$ alkyl, —$SO_2$—$N(C_1$-$C_8$ alkyl$)_2$ and —$SO_3H$, any of which may be optional substituted;

$R_9$ and $R_{12}$ are independently selected from the group consisting of H, $C_1$-$C_8$ alkyl, $C_2$-$C_8$ alkenyl, $C_2$-$C_8$ alkynyl, $C_1$-$C_8$ alkoxy, —OC(O)—$C_1$-$C_8$ alkyl, —OC(O)—$C_6$-$C_{12}$ aryl, $C_3$-$C_{12}$ cycloalkyl, $C_6$-$C_{12}$ aryl, $C_2$-$C_{11}$ heterocyclo alkyl $C_2$-$C_9$ heteroaryl and hydroxy, any of which may be optionally substituted; and $R_{10}$ and $R_{11}$ are independently selected from the group consisting of H, $C_1$-$C_8$ alkyl, $C_6$-$C_{12}$ aryl, $C_7$-$C_{12}$ arylalkyl, $C_2$-$C_9$ heteroaryl, $C_3$-$C_{17}$ heteroaryl-alkyl, $C_3$-$C_{12}$ cycloalkyl, $C_4$-$C_{20}$ cycloalkyl-alkyl, $C_2$-$C_{11}$ heterocycloalkyl and $C_3$-$C_{19}$ heterocycloalkyl-alkyl, any of which may be optional substituted;

or a prodrug, a pharmaceutically acceptable salt, or a pharmaceutically active metabolite.

A more specific embodiment of the compounds of formula (II) is where $R_2$ is aryl or heteroaryl, and more preferably is an optionally substituted phenyl, $R_3$-$R_8$ are independently selected from H, alkyl, haloalkyl, halo, alkoxy, hydroxy, CN, amino, alkylamino, dialkylamino, alkylthio or —$SO_2NH_2$, A is O, $R_9$ and $R_{12}$ are independently selected from the group consisting of H, alkyl, and hydroxy, where H and hydroxy are the most preferable, and $R_{10}$ and $R_{11}$ are independently H or alkyl, but are preferably H, or a prodrug, a pharmaceutically acceptable salt or a pharmaceutically active metabolite thereof.

A preferred embodiment of the method of this invention is where the compounds of formula (A) are defined by:

$R_1$ is selected from the group consisting of $C_1$-$C_8$ alkyl, $C_2$-$C_8$ alkenyl, $C_2$-$C_8$ alkynyl, $C_3$-$C_{12}$ cycloalkyl, $C_6$-$C_{12}$ aryl, $C_2$-$C_9$ heteroaryl, CN and —C($NR_{10}R_{11}$)=N—$R_{12}$, any of which may be optionally substituted;

$R_2$ is selected from the group consisting of $C_1$-$C_8$ alkyl, $C_2$-$C_8$ alkenyl, $C_2$-$C_8$ alkynyl, $C_3$-$C_{12}$ cycloalkyl, $C_6$-$C_{12}$ aryl and $C_2$-$C_9$ heteroaryl, any of which may be optionally substituted;

$R_3$-$R_8$ are independently selected from the group consisting of H, halo, hydroxy, $C_1$-$C_8$ alkyl, $C_1$-$C_8$ haloalkyl, acyl, $C_2$-$C_9$ heteroaryl, $C_6$-$C_{12}$ aryl, $C_3$-$C_{12}$ cycloalkyl, $C_2$-$C_{11}$ heterocycloalkyl, $C_7$-$C_{12}$ arylalkyl, $C_3$-$C_{17}$ heteroaryl-alkyl, CN, amino, $C_1$-$C_8$ alkylamino, $C_1$-$C_8$ dialkylamino, Nitro, —COOH, —C(O)—$C_1$-$C_8$ alkyl, —C(O)—$C_6$-$C_{12}$-aryl, $C_1$-$C_8$ alkoxy, $C_1$-$C_8$ haloalkoxy, mercapto, $C_1$-$C_8$ alkylthio, $C_6$-$C_{12}$ arylthio, amido, sulfamido, —$SO_2$—$C_1$-$C_8$ alkyl, $C_1$-$C_8$ alkylamido, $C_1$-$C_8$ dialkylamido, —$SO_2NH$—$C_1$-$C_8$ alkyl, —$SO_2$—$N(C_1$-$C_8$ alkyl$)_2$ and —$SO_3H$, any of which may be optional substituted;

$R_9$ and $R_{12}$ are independently selected from the group consisting of H, $C_1$-$C_8$ alkyl, $C_2$-$C_8$ alkenyl, $C_2$-$C_8$ alkynyl, $C_1$-$C_8$ alkoxy, —OC(O)—$C_1$-$C_8$ alkyl, —OC(O)—$C_6$-$C_{12}$ aryl, $C_3$-$C_{12}$ cycloalkyl, $C_6$-$C_{12}$ aryl, $C_2$-$C_{11}$ heterocyclo alkyl $C_2$-$C_9$ heteroaryl and hydroxy, any of which may be optionally substituted;

$R_{10}$ and $R_{11}$ are independently selected from the group consisting of H, $C_1$-$C_8$ alkyl, $C_6$-$C_{12}$ aryl, $C_7$-$C_{12}$ arylalkyl, $C_2$-$C_9$ heteroaryl, $C_3$-$C_{17}$ heteroaryl-alkyl, $C_3$-$C_{12}$ cycloalkyl, $C_4$-$C_{20}$ cycloalkyl-alkyl, $C_2$-$C_{11}$ heterocycloalkyl and $C_3$-$C_{19}$ heterocycloalkyl-alkyl, any of which may be optional substituted;

or a prodrug, a pharmaceutically acceptable salt, or a pharmaceutically active metabolite.

A more specific embodiment of the method of this invention is where the compounds of formula (A) are defined by $R_1$ being selected from the group consisting of CN, optionally substituted alkenyl and —C($NR_{10}R_{11}$)=$NR_{12}$, $R_2$ is aryl or heteroaryl, and preferably an optionally substituted phenyl, A is O, $R_9$ and $R_{12}$ are independently H, alkyl and hydroxy, where H and hydroxyl are most preferred, and $R_{10}$ and $R_{11}$ are independently H or $C_1$-$C_8$ alkyl, but preferably H, or a prodrug, a pharmaceutically acceptable salt or a pharmaceutically active metabolite thereof.

Another embodiment of the method of this invention is where an effective amount of one or more additional HIV inhibitors is co-administered with the 1,2-dihydroquinoline compound of formula (A), and the additional HIV inhibitors are administered in a single dosage form with the compound of formula (A). Preferably the additional HIV inhibitors are selected from the group consisting of reverse transcriptase inhibitors, non-nucleoside reverse transcriptase inhibitors and retroviral protease inhibitors. Retroviral protease inhibitors are the most preferred, particularly if they are capable of inhibiting the metabolism of any of the other HIV inhibitors that are co-administered, such as retonavir.

In a further embodiment of the invention, there is provided a method for treating or preventing retrovirus-associated cancer comprising administering to a subject an effective amount of a 1,2-dihydroquinoline derivative of the present invention.

The present invention also provides a method for screening for candidate 1,2-dihydroquinoline derivatives having RNase H, polymerase and/or HIV reverse transcriptase modulatory activity.

Preferred compounds of the present invention include:

1-(4-chlorobenzoyl)-2-vinyl-1,2-dihydroquinoline of formula (I); and 1-(4-chlorobenzoyl)-6-methyl-1,2-dihydroquinoline-2-carbonitrile;

1-(4-chlorobenzoyl)-N'-hydroxy-6-methyl-1,2-dihydroquinoline-2-carboximidamide;

4,7-dichloro-1-(4-fluorobenzoyl)-1,2-dihydro-quinoline-2-carbonitrile;

1-(4-chlorobenzoyl)-6-nitro-1,2-dihydroquinoline-2-carbonitrile;

6-chloro-1-(4-chlorobenzoyl)-1,2-dihydroquinoline-2-carbonitrile;

1-(4-chlorobenzoyl)-7-methyl-1,2-dihydroquinoline-2-carbonitrile;

5-chloro-1-(4-chlorobenzoyl)-1,2-dihydroquinoline-2-carbonitrile; and 4,7-dichloro-1-benzoyl-1,2-dihydroquinoline-2-carbonitrile of formula (II).

The compounds of this invention contain an asymmetric carbon atom and some of the compounds of this invention may contain two or more asymmetric centers and may thus give rise to stereoisomers, such as enantiomers and diastereomers. The stereoisomers of the instant invention are named according to the Cahn-Ingold-Prelog System. While shown without respect to stereochemistry in formulas (I), (II) and (A), the present invention includes all the individual possible stereoisomers; as well as the racemic mixtures and other mixtures of R and S stereoisomers (scalemic mixtures which are mixtures of unequal amounts of enantiomers) and pharmaceutically acceptable salts thereof. It should be noted that stereoisomers of the invention having the same relative configuration at a chiral center may nevertheless have different R and S designations depending on the substitution at the indicated chiral center.

The compounds of the current invention may be alkene diastereomers. The alkene diastereomers can be designated using the (E)-(Z) system. One skilled in the art will be familiar with this system of nomenclature. Where alkene compounds are disclosed without stereospecifity it is intended that both of the diastereomers are encompassed.

If an inventive compound is a base, a desired salt may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid or ethanesulfonic acid, or the like.

If an inventive compound is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

A "prodrug" is intended to mean a compound that is converted under physiological conditions or by solvolysis or metabolically to a specified compound that is pharmaceutically active. A prodrug may be a derivative of one of the compounds of this invention that contains a moiety, such as for example —$CO_2R$, —$PO(OR)_2$ or —C=NR, that may be cleaved under physiological conditions or by solvolysis. Any suitable R substituent may be used that provides a pharmaceutically acceptable solvolysis or cleavage product. A prodrug containing such a moiety may be prepared according to conventional procedures by treatment of a compound of this invention containing, for example, an amido, carboxylic acid, or hydroxyl moiety with a suitable reagent. A "pharmaceutically active metabolite" is intended to mean a pharmacologically active compound produced through metabolism in the body of a specified compound. Prodrugs and active metabolites of compounds of this invention of the above-described Formulas may be determined using techniques known in the art, for example, through metabolic studies. See, e.g., "Design of Prodrugs," (Bundgaard, ed.), 1985, Elsevier Publishers B.V., Amsterdam, The Netherlands. A "pharmaceutically acceptable salt" is intended to mean a salt that retains the biological effectiveness of the free acids and bases of a specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methane-sulfonates (mesylates), propanesulfonates, naphthalene-1-sulfonates, naphthalene-2-sulfonates, and mandelates. In the case of compounds or salts that are solids it is understood by those skilled in the art that the inventive compounds or salts may exist in different crystal forms, all of which are intended to be within the scope of the present invention and specified formulas.

An inventive compound of formula (A), (I) or (II), or a pharmaceutically acceptable salt, prodrug, or active metabolite thereof, may be administered as a pharmaceutical composition in any pharmaceutical form recognizable to the skilled artisan as being suitable. Suitable pharmaceutical forms include solid, semisolid, liquid, or lyophilized formulations, such as tablets, powders, capsules, suppositories, suspensions, liposomes, and aerosols. Pharmaceutical compositions of the invention may also include suitable excipients, diluents, vehicles, and carriers, as well as other pharmaceutically active agents, depending upon the intended use or mode of administration. In preferred embodiments, the inventive pharmaceutical compositions are delivered orally. Acceptable methods of preparing suitable pharmaceutical forms of the pharmaceutical compositions may be routinely determined by those skilled in the art. For example, pharmaceutical preparations may be prepared following conventional techniques of the pharmaceutical chemist involving steps such as mixing, granulating, and compressing when necessary for tablet forms, or mixing, filling, and dissolving the ingredients as appropriate, to give the desired products for oral, parenteral, topical, intravaginal, intranasal, intrabronchial, intraocular, intraaural, and/or rectal administration.

The compounds (active ingredients) may be formulated into solid oral dosage forms which may contain, but are not limited to, the following inactive ingredients: diluents (i.e., lactose, corn starch, microcrystalline cellulose), binders (i.e., povidone, hydroxypropyl methylcellulose), disintegrants (i.e., crospovidone, croscarmellose sodium), lubricants (i.e., magnesium stearate, stearic acid), and colorants (FD&C lakes or dyes). Alternatively, the compounds may be formulated into other oral dosage forms including liquids, suspensions, emulsions, or soft gelatin capsules, with each dosage form having a unique set of ingredients.

Solid or liquid pharmaceutically acceptable carriers, diluents, vehicles, or excipients may be employed in the pharmaceutical compositions. Illustrative solid carriers include starch, lactose, calcium sulfate dihydrate, terra alba, sucrose, talc, gelatin, pectin, acacia, magnesium stearate, and stearic acid. Illustrative liquid carriers include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., solution), or a nonaqueous or aqueous liquid suspension. A dose of the pharmaceutical composition contains at least a therapeutically effective amount of the active compound (i.e., a compound of formulas (A), (I) and (II), or a pharmaceutically acceptable salt, prodrug, or pharmaceutically active metabolite thereof), and preferably is made up of one or more pharmaceutical dosage units. The selected dose may be administered to a mammal, for example, a human patient, by any known or suitable method of administering the dose, including: topically, for example, as an ointment or cream; orally; rectally, for example, as a suppository; parenterally by injection; or continuously by intravaginal, intranasal, intrabronchial, intraaural, or intraocular infusion. A "therapeutically effective amount" is intended to mean the amount of an inventive agent that, when administered to a mammal in need thereof, is sufficient to effect treatment for disease conditions associated with HIV infections. The amount of a given compound of the invention that will be therapeutically effective will vary depending upon factors such as the particular compound, the disease condition and the severity thereof, and the identity of the mammal in need thereof, which amount may be routinely determined by artisans.

The compounds of the present invention modulate, and preferably inhibit, RNase H nuclease activity. RNase H is an enzyme responsible for the removal of RNA primers from leading and lagging strands during DNA synthesis. It is an important enzyme for the replication of bacterial, viral and human genomes. HIV reverse transcriptase has an RNase H domain at the C-terminus of its p66 subunit. Accordingly, the compounds of the present invention modulate, and preferably inhibit, HIV reverse transcriptase. The ability of the compounds of the present invention to inhibit RNase H, and more particularly HIV reverse transcriptase, may be determined by any means known in the art.

Preferably, the RNase H/HIV reverse transcriptase modulatory activity of the compounds of the present invention may be determined by the methods described in copending U.S. Provisional Patent Application No. 60/436,125, filed Dec. 19, 2002 and PCT International Publication No. WO/2004/059012, filed Dec. 22, 2003 for ASSAY FOR RNase ACTIVITY of Olson et al., incorporated herein by reference in its entirety. Specifically, the modulatory activity of a hydantoin derivative of the present invention may be determined by hybridizing a target nucleic acid to a fluorescently labeled oligonucleotide probe complementary to the target nucleic acid and containing a fluorophor at one terminus and a quenching group at the other terminus to obtain a probe-target hybrid, wherein (i) the unhybridized probe adopts a conformation that places the fluorophor and quencher in such proximity that the quencher quenches the fluorescent signal of the fluorophor, and (ii) the formation of the probe-target hybrid causes sufficient separation of the fluorophor and quencher to reduce quenching of the fluorescent signal of the fluorophor. Next, a first and second sample containing the probe-target hybrid are prepared. The probe-target hybrid of the first sample is then contacted with an RNase H enzyme (such as HIV reverse transcriptase) in an amount sufficient to selectively cleave the target nucleic acid and thereby release the intact probe. The probe-target hybrid of the second sample is also contacted with the RNase H enzyme in an amount sufficient to selectively cleave the target nucleic acid and thereby release the intact probe in the presence of a compound of the present invention. The release of the probe in each sample may then be detected by measuring the decrease in the fluorescent signal of the fluorophor as compared to the signal of the probe-target hybrid. A comparison of the rate of the decrease in the fluorescent signal of the fluorophor in the two samples is made to determine whether there is a difference in the rate of the decrease in the two samples. A difference in the rate of decrease in the samples indicates that the 1,2-dihydroquinoline compound is a modulator of RNase H/HIV reverse transcriptase. This method is also useful to identify 1,2-dihydroquinoline derivatives of the present invention, wherein the candidate derivatives are screened for their ability to modulate RNase/HIV reverse transcriptase activity.

The method of the present invention for modulating, and preferably inhibiting, the nuclease activity of RNase, comprises contacting RNase, either in vitro or in vivo, with the compounds of the present invention. The RNase H modulatory activity, and particularly inhibitory activity, of the compounds of the present invention indicates that they are useful for inhibiting the replication of HIV in a cell infected with HIV. It further indicates that the compounds are useful in the prevention and treatment of HIV and AIDS.

In addition, the compounds of the present invention may be useful for treating other microbial infections, including bacterial and viral infections, wherein the bacteria or virus relies on RNase H nuclease activity for replication.

The compounds may further be useful for treating certain cancers, and particularly retrovirus associated adenocarcinomas, such as breast cancer. See U.S. Pat. No. 5,223,490, incorporated herein by reference in its entirety.

The method of the present invention for modulating, and preferably inhibiting, polymerase activity, comprises contacting polymerase, either in vitro or in vivo, with the compounds of the present invention. The polymerase modulatory activity, and particularly inhibitory activity, of the compounds of the present invention indicates that they are useful for inhibiting the replication of HIV in a cell infected with HIV. It further indicates that the compounds are useful in the prevention and treatment of HIV and AIDS.

In addition, the compounds of the present invention may be useful for treating other viral infections, wherein the virus relies on RDDP polymerase activity for replication.

The compounds may further be useful for treating certain cancers, and particularly retrovirus associated adenocarcinomas, such as breast cancer. See U.S. Pat. No. 5,223,490, incorporated herein by reference in its entirety.

The 1,2-dihydroquinoline compounds of the present invention preferably inhibit polymerase and HIV reverse transcriptase with IC50 values of 1 to 300 µM. In one embodiment the compounds of the present invention inhibit the polymerase activity of HIV reverse transcriptase with the IC50 values shown in Table I.

For retrovirus-associated cancer, additional anti-cancer agents may be administered. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the compounds of the present invention and other agent(s) at the same time. This may be achieved by contacting the cell with a single composition or pharmacological formulation that includes both agents, or by contacting the cell with two distinct compositions or formulations, at the same or different time, wherein one composition includes the 1,2-dihydroquinoline derivative and the other includes the second agent(s).

The compounds of the present invention can be administered as the sole therapeutic agent or they can be administered in combination with one or more other therapeutic agents. Other useful therapeutic agents are compounds that have immunomodulating activity, antiviral or antiinfective activity and vaccines. Therapeutic agents with antiviral activity are encompassed within the following classifications: retroviral protease inhibitors (for example ritonavir, Ro-31-8959, SC-52151, KNI-227 and KNI-272), non-nucleoside reverse transcriptase inhibitors (for example Sustiva, nevirapine, delavirdine, R82193 and L-697,661) reverse transcriptase inhibitors (for example AZT, ddI, 3TC, d4T, abacavir and ddC). Ritonavir is an ideal therapeutic agent for combination therapy because besides being a potent protease inhibitor it is also known to be a potent inhibitor of cytochrome P450 monooxygenase, specifically the CYP3A, CYP2C9 and CYP2D6 isoforms. Thus, therapeutic agents administered in combination with ritonavir may experience an increase in half-life, which usually results in an increase in efficacy.

Polymerase Inhibitory Activity of the Compounds of the Invention

The RNA dependent DNA polymerase (RDDP) activity of HIV RT was evaluated using polyrA-oligodT$_{12-18}$ as the template-primer allowing for TTP incorporation (Telesnitsky, A., Blain, S, and Goff, S. P. (1995) *Methods in Enzymology* 262, 347-362 and Goff, S, Traktman, P., and Baltimore, D (1981) *J. Virology* 38, 239). The Michaelis Constants for HIV RT RDDP were first determined for the two substrates TTP and polyrA-oligodTi2-18 independently. The $K_m$-values for TTP and polyrA-oligodT$_{12-18}$ were determined to be 7.1 µM and 5.4 nM, respectively.

HIV Reverse transcriptase (RT) 66/p51 at a concentration of 10800 units/mg (19.6 µM following stabilization in 50% glycerol) was obtained from Worthington. The template primer used was polyrA-oligodT12-18 at 4.47 µM as substrate was obtained from Pharmacia, as well as TTP (thymidine tri-phosphate), which was stored at a concentration of 1 mM. $^{33}$P TTP at 10 µCi/µl (3000 Ci/mmol) and 3.3 µM was obtained from NEN/DuPont. A 5×HIV RT buffer was prepared with the 1× final concentration being 50 mM Tris-HCl (pH 8.5), 6 mM MgCl$_2$, 80 mM KCl, 1 mM DTT (dithiotrheitol), 0.05% Triton X-100, 0.05 mg/ml BSA (bovine serum albumin). The wash buffer consisted of 0.5 M Na$_2$HPO$_4$ (pH 7.0). Filter plates were obtained from Millipore Corp. The scintillant used was Optiphase Supermix from Wallac/Perkin Elmer, manufactured by Fisher Chemicals.

A 25 µl reaction was generated from the reagents above in the following manner: An enzyme mix (consisting of 2.5× reaction buffer, 100% DMSO, and 25 fmol of HIV RT) and a substrate mix (consisting of 0.1625 mM TTP, 0.00725 µM $^{33}$P TTP [0.00725 µCi] and 0.015 µM polyrA-dT was generated. Both mixes were stable for up to 1 hour at room temperature. The enzyme, reverse transcriptase was added to the enzyme mix after the other constituents of the enzyme mix were made homogeneous. For the reaction, 5 µl of test compound (or 15% DMSO) was mixed with 10 µl enzyme mix and 10 µl substrate mix and the final mixture was incubated for 2 hours at room temperature. EDTA controls contained 10 fmol enzyme and was used to determine the non-specific retention of the radio-labeled nucleotide in the filter plate, i.e. it is a mock reaction. The reaction was stopped after 2 hours by the addition of 100 µl of 50 mM EDTA. The filter plates were prewashed with 200 µl of wash buffer using a vacuum applied to the filter. 100 µl of each sample was filtered through the filter plates and then they were washed 3 times with 200 µl of wash buffer. 1 microliter of reaction mix was spotted onto a filter to determine specific activity of the reaction mix. The plates were allowed to dry for 30 minutes to 60 minutes. Scintillant was added and the counts per minute were determined in a Wallac Micro-Beta counter.

One unit of HIV RT is defined as that amount of enzyme that results in the incorporation of 1 nmol of TMP (thymidine mono-phosphate) into an acid insoluble precipitate in 10 minutes at 37° C. using polyrA oligodT$_{12-18}$ as the template primer (Worthington Enzyme Corporation Catalogue year 2001).

An enzyme mix and a substrate mix was generated. To prepare the enzyme mix, the enzyme was added to the enzyme mix last to ensure it was buffered and maintained in a reduced state (presence of dithiothreitol, DTT). It is critical not to vortex the enzyme mix after the addition of enzyme. Rather, the enzyme was mixed into solution by gentle inversion or pipetting or mixing. To generate a homogeneous mixture of the substrate solution gentle vortexing was used. The enzyme solution was added to the plates containing compounds. 5 ul of 15% DMSO was added to the non-compound containing samples. DMSO at a concentration of 3% will stimulate HIV RT RDDP activity up to 3-fold. Without the addition of DMSO in the positive control samples an underestimate of the inhibitory activity of the compound being assayed will be obtained. The enzyme was then incubated with the compound for 15 min at room temperature (~23° C.) prior to the addition of the substrate mix. The enzyme was allowed to incubate with the substrate for 2 h at room temperature (~23° C.). Under these conditions enzyme reaction was linear for >4 h and utilizes less than 7% of the available substrates (TTP and polyrA-oligodT$_{12-18}$). The assays were stopped by the addition of 100 ul of 50 mM EDTA and 100 ul of each sample was subjected to filtration in the Millipore DE MADEN OB50 plates. These plates were washed to remove unincorporated radiolabeleled nucleotides, dried and subjected to counts per minute (cpm) measurement in the Wallac Micro-Beta counter after the addition of scintillant. The quantity of TTP incorporated was then determined by the specific activity (S.A.) of the reaction mix, as discussed in the results section below, to ensure that less than 10% of the available substrates were consumed in the reaction and ensured linearity of the enzyme reaction. In addition, a mock reaction was included as a control. This reaction contained all of the assay components but contained the addition of 100 ul of 50 mM EDTA at the initiation of the reaction. This mock reaction control determined the quantity of background counts (cpm) in the reaction. $IC_{50}$-values <10 ug/ml or 10 μM were considered active (See Table I above for $IC_{50}$-values).

The instrument used for quantitation was a Wallac Micro-Beta linked to a Windows based compatible desktop computer. The specific activity (S.A.) of the reaction mix was defined as cpm/pmol of TTP in the mix. (cpm—counts per minute in scintillation counting.) As noted above, 1 ul from a reaction was spotted in triplicate onto a filter the Millipore DE MADEN OB50 plates. This filter was not subjected to the washing procedure. It was used to accurately reflect the concentration of radioactivity per pmol of nucleotide in the reaction mixture. To determine specific activity, the following calculation was used S.A.=total cpm per ul divided by pmol TTP per ul, which provides cpm/pmol of TTP in the reaction. The $K_m$-value was ~7 μM, 6.5 μM concentration of TTP is used in the reaction.

In the reaction the incorporation of nucleotide by cpm was measured. This was converted to pmol of nucleotide incorporated by dividing the total number of cpms in the reaction by the S.A. of that reaction Sample Calculation The pmol of nucleotides incorporated in reaction X was calculated as follows: Cpm of reaction X divided by a given unit of time which equals pmol of TTP incorporated in reaction X in a given unit time. The S.A. of the reaction for the HIV RT assay was: S.A.=10,000 cpm/(6.5 pmol/ul)=1538.46 cpm/pmol. The final concentration of TTP was 6.5 uM (6.5 pmol/ul). 5500 cpms were measured in reaction X, but only 100 ul of 125 ul of the reaction was transferred to the filter plate from the reaction plate. The background retention of radiolabeled nucleotide was determined to be 125 cpm (5500 cpm–125 cpm is 5375 cpm; =5375 cpm×(125/100) =6718.75 cpm is the total for reaction X=6718.75 cpm/ (1538.46 cpm/pmol)=4.36 pmol of TTP was incorporated. The $IC_{50}$-values for the compounds of the invention are shown in Table I below.

The 1,2-dihydroquinoline compounds of the present invention preferably inhibit RNase H and HIV reverse transcriptase with IC50 values of 1 to 100 μM. In one embodiment, the compounds of the present invention inhibit HIV reverse transcriptase with the IC50 values shown in Table I below:

TABLE I

| Example | MW | IC50 |
|---------|-------|------|
| 1 | 308.8 | 20.6 |
| 2 | 341.8 | 25.4 |
| 3 | 295.8 | 76.0 |
| 4 | 347.2 | 19.0 |
| 5 | 339.8 | 0.3 |
| 6 | 329.2 | 4.1 |
| 7 | 308.8 | 6.7 |
| 8 | 329.2 | 49.6 |
| 9 | 329.2 | 86.0 |

As reference compounds, Efavirenz was used which had an $IC_{50}$-value of <1 μM and AZT was used, which had an $IC_{50}$-value of <0.2 μM.

The compounds of the invention can be synthesized according to the reaction schemes presented hereafter. $R_1$-$R_8$ and A are as defined previously.

Scheme I

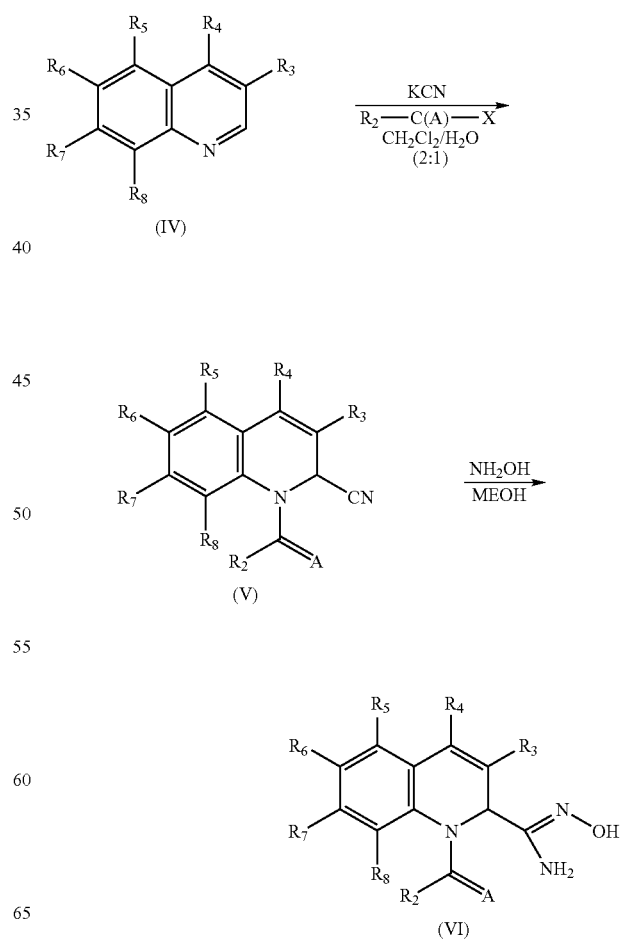

Scheme 11

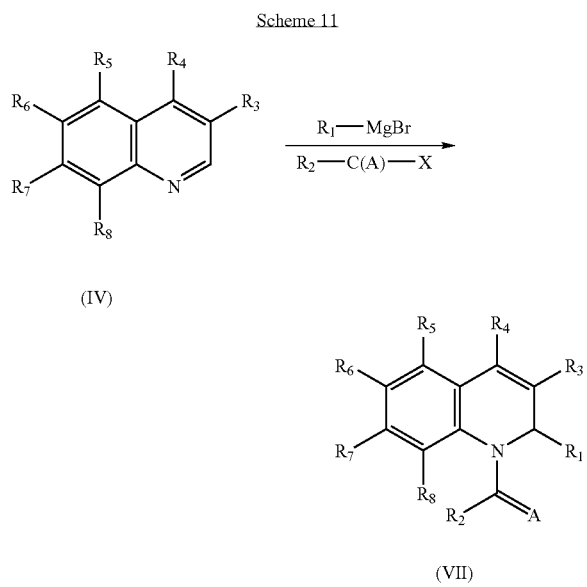

Scheme I illustrates the general synthethic pathway for making compounds of formula (II), 2-carbonitrile and 2-carboximidamide substituted 1,2-dihydroquinoline that has been further alkylated at the 1-position. The quinoline compound of formula (IV) is reacted with a cyanide source, such as KCN, to add a cyano group at the 2-position. An electrophilic reagent of the structure $R_2$—C(A)—X, wherein X is a leaving group, that is capable of undergoing nucleophilic attack by a secondary amine is also employed to add the $R_2$—C(A)-group to the quinoline nitrogen. This reaction gives the 2-carbonitrile-1,2-dihydroquinoline of formula (V). One skilled in the art would know of typical reagents to employ that are capable of undergoing nucleophilic substitution at the quinoline nitrogen, such as acid halides, sulfonyl halides or anhydride. The compounds of formula (V) can possess RNase H inhibitory activity, but can be further modified by reacting them with hydroxylamine to obtain the corresponding carboximidamide of formula (VI). These carboximidamide compounds can be further alkylated at the oxime or amine position. The literature is replete with reagents and reaction conditions that can be used to effect such reactions. Those skilled in the art would be knowledgeable of this literature.

Scheme II illustrates the general synthetic pathway for obtaining formula (I) compounds, 2-substituted 1,2-dihydroquinoline compounds, that have also been alkyated at the 1-position. The quinoline of formula (IV) is reacted with an organometallic reagent, such as organolithium reagent or a Grignard reagent, and then subsequently an electrophilic reagent, such as an acid halide, sulfonyl halide or anydride, to obtain the compound of formula (VII).

The following examples provide illustrative experimental procedures and are not limitative of scope.

EXAMPLE 1

Synthesis of 1-(4-chlorobenzoyl)-6-methyl-1,2-dihydroquinoline-2-carbonitrile

To a biphasic mixture of 6-methylquinoline (1.0 g) in dichloromethane (9 mL) and potassium cyanide (1.37 g) in water (4 mL) was added 4-chlorobenzoyl chloride (1.78 mL). The reaction mixture was stirred at ambient conditions overnight. The reaction mixture was then filtered and the filtrate washed successively with water, 1N hydrochloric acid, 1N sodium hydroxide solution and water. The organic layer was dried over sodium sulfate, filtered and concentrated in vacuo. The crude product was purified by liquid chromatography (gradient elution of acetonitrile (0.02% trifluoroacetic acid)/water (0.02% trifluoroacetic acid) through a reverse phase C 18 column) to give the titled compound (118 mg product, 5% yield) as a foam. $(M+H)^+$–309.

EXAMPLE 2

Synthesis of 1-(4-chlorobenzoyl)-N'-hydroxy-6-methyl-1,2-dihydroquinoline-2-carboximidamide To a solution of 1-(4-chlorobenzoyl)-6-methyl-1,2-dihydroquinoline-2-carbonitrile (200 mg) in methanol (1 mL) was added cold 1M hydroxylamine in methanol (971 μL). The reaction mixture was warmed to ambient conditions and stirred overnight. The methanol is removed in vacuo and the crude product is purified by liquid chromatography (gradient elution of acetonitrile (0.02% trifluoroacetic acid)/water (0.02% trifluoroacetic acid) through a reverse phase C18 column) to give the titled compound (25 mg, 11% yield) as a pale yellow solid. $(M+H)^+$–342.

EXAMPLE 3

Synthesis of 1-(4-chlorobenzoyl)-2-vinyl-1,2-dihydroquinoline

A solution of vinyl magnesium bromide (4.65 mL in 1M THF solution) under nitrogen gas at ambient conditions is treated with quinoline dropwise. The reaction mixture is warmed to 40° C. and stirred for 1 h. The reaction mixture is then allowed to attain ambient conditions and 4-chlorobenzoyl chloride (591 μL) is then added dropwise and reaction mixture stirred overnight. The reaction mixture is then cooled to 0° C. and quenched with saturated aqueous ammonium chloride solution. The reaction mixture is then partitioned between diethyl ether and water and the organic layer is washed successively with 1N hydrochloric acid and 1N sodium hydroxide solution and then dried over sodium sulfate. The organic solvent is removed under reduced pressure and the crude product is purified by liquid chromatography (gradient elution of acetonitrile (0.02% trifluoroacetic acid/ water (0.02% trifluoroacetic acid) through a reverse phase. $(M+H)^+$–296.

EXAMPLE 4

Synthesis of 4,7-dichloro-1-(4-fluorobenzoyl)-1,2-dihydroquinoline-2-carbonitrile This compound was synthesized as per Example 1 employing 4-fluorobenzoyl chloride and 4,7-dichloroquinoline as starting reactants. M.P.=168-170.

EXAMPLE 5

Synthesis of 1-(4-chlorobenzoyl)-6-nitro-1,2-dihydroquinoline-2-carbonitrile

This compound was synthesized as per Example 1 employing 4-chlorobenzoyl chloride and 6-nitroquinoline as starting reactants. $(M+H)^+$–340.

EXAMPLE 6

Synthesis of 6-chloro-1-(4-chlorobenzoyl)-1,2-dihydroquinoline-2-carbonitrile This compound was synthesized as per Example 1 employing 4-chlorobenzoyl chloride and 6-chloroquinoline as starting reactants. $(M+H)^+$–330.

EXAMPLE 7

Synthesis of 1-(4-chlorobenzoyl)-7-methyl-1,2-dihydroquinoline-2-carbonitrile This compound was synthesized as per Example 1 employing 4-chlorobenzoyl chloride and 7-methylquinoline as starting reactants. $(M+H)^+$–309.

EXAMPLE 8

Synthesis of 5-chloro-1-(4-chlorobenzoyl)-1,2-dihydroquinoline-2-carbonitrile This compound was synthesized as per Example 1 employing 4-chlorobenzoyl chloride and 5-chloroquinoline as starting reactants. $(M+H)^+$–329.

EXAMPLE 9

Synthesis of 4,7-dichloro-1-benzoyl-1,2-dihydroquinoline-2-carbonitrile

This compound was synthesized as per Example 1 employing benzoyl chloride and 6-chloroquinoline as starting reactants.

The invention is not to be limited except as set forth in the following claims.

What is claimed is:

1. A compound of formula (A):

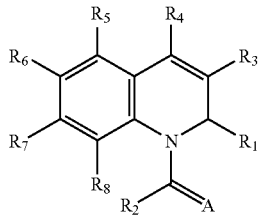

wherein:
$R_1$ is selected from (a) alkyl, alkenyl, alkynyl, cycloalkyl, aryl, and heteroaryl or (b) CN and —$C(NR_{10}R_{11})$=N—$R_{12}$, any of which may be optionally substituted;
$R_2$ is aryl, which is substituted;
$R_3$ and $R_5$-$R_8$ are independently selected from H, halo, hydroxy, alkyl, haloalkyl, acyl, aryl, cycloalkyl, arylalkyl, heteroarylalkyl, CN, amino, alkylamino, dialkylamino, nitro, —$CO_2H$, —C(O)-alkyl, —C(O)-aryl, alkoxy, haloalkoxy, mercapto, alkylthio, arylthio, amido, —$SO_2NH$, —$SO_3H$, —$SO_2NH$-alkyl, —$SO_2N$-(alkyl)$_2$, aryloxy and heteroaryloxy, any of which may be optionally substituted;
$R_4$ is selected from H, halo, hydroxyl, alkyl, haloalkyl, acyl, aryl, cycloalkyl, arylalkyl, heteroarylalkyl, CN, amino, alkylamino, nitro, —$CO_2H$, —C(O)-alkyl, —C(O)-aryl, alkoxy, haloalkoxy, mercapto, alkylthio, arylthio, amido, —$SO_2NH$, —$SO_3H$, —$SO_2NH$-alkyl, —$SO_2N$-(alkyl)$_2$, aryloxy and heteroaryloxy, any of which may be optionally substituted;
$R_{10}$ and $R_{11}$ are independently selected from H, alkyl, aryl, arylalkyl, heteroaryl, heteroarylalkyl, cycloalkyl, cycloalkylalkyl, heterocycloalkyl and heterocycloalkylalkyl, any of which may be optionally substituted;
$R_9$ and $R_{12}$ are independently selected from alkoxy, —OC(O)-alkyl, —OC(O)-aryl, cycloalkyl, aryl, heterocycloalkyl, heteroaryl and hydroxy, any of which may be optionally substituted; and
A is O, $NR_9$ or S;
or a pharmaceutically acceptable salt thereof,
provided that $R_1$ is not alkyl when $R_2$ is pyridine;
provided that at least one of $R_3$-$R_8$ is not H or F when A is O, $R_1$ is (b) and $R_2$ is a phenyl ring, a phenyl ring substituted at the para position with halo, —CN, —$OCH_3$, —$CF_3$ or —$CO_2CH_3$, a quinoline or an ethylene substituted with a phenyl ring or a 3,4-methylenedioxyphenyl moiety; and
provided that $R_4$ is not methyl when $R_3$ and $R_5$-$R_8$ are H, A is O, $R_1$ is (b) and $R_2$ is 4-chlorophenyl.

2. A compound of formula (I):

wherein:
$R_1$ is selected from alkyl, alkenyl, alkynyl, cycloalkyl, aryl, and heteroaryl any of which may be optionally substituted;
$R_2$ is aryl, which is substituted;
$R_3$ and $R_5$-$R_8$ are independently selected from H, halo, hydroxyl, alkyl, haloalkyl, acyl, aryl, cycloalkyl, arylalkyl, heteroaryl-alkyl, CN, amino, alkylamino, dialkylamino, nitro, —COOH, —C(O)-alkyl, —C(O)-aryl, alkoxy, haloalkoxy, mercapto, alkylthio, arylthio, amido, sulfamido, sulfonylalkyl, alkylamido, dialkylamido, —$SO_2NH$-alkyl, —$SO_2N$-(alkyl)$_2$ and —$SO_3H$, any of which may be optionally substituted;
$R_4$ is selected from H, halo, hydroxyl, alkyl, haloalkyl, acyl, aryl, cycloalkyl, arylalkyl, heteroaryl-alkyl, CN, amino, alkylamino, nitro, —COOH, —C(O)-alkyl, —C(O)-alkyl, alkoxy, haloalkoxy, mercapto, alkylthio, arylthio, amido, sulfamido, sulfonylalkyl, alkylamido, dialkylamido, —$SO_2NH$-alkyl, —$SO_2N$-(alkyl)$_2$ and —$SO_3H$, any of which may be optionally substituted;
A is O, $NR_9$ or S;
$R_9$ is selected from alkoxy, —OC(O)-alkyl, —OC(O)-aryl, cycloalkyl, aryl, heterocycloalkyl, heteroaryl and hydroxy, any of which may be optionally substituted; and
or a pharmaceutically acceptable salt thereof;
provided that $R_1$ is not alkyl when $R_2$ is pyridine.

23

3. The compound of claim 2, wherein:

$R_1$ is selected from $C_1$-$C_8$ alkyl, $C_2$-$C_8$ alkenyl, $C_2$-$C_8$ alkynyl, $C_3$-$C_{12}$ cycloalkyl, $C_6$-$C_{12}$ aryl, and $C_2$-$C_9$ heteroaryl, any of which may be optionally substituted;

$R_2$ is $C_6$-$C_{12}$ aryl, which is substituted;

$R_3$ and $R_5$-$R_8$ are independently selected from H, halo, hydroxy, $C_1$-$C_8$ alkyl, $C_1$-$C_8$ haloalkyl, acyl, $C_6$-$C_{12}$ aryl, $C_3$-$C_{12}$ cycloalkyl, $C_7$-$C_{12}$ arylalkyl, $C_3$-$C_{17}$ heteroaryl-alkyl, CN, amino, $C_1$-$C_8$ alkylamino, $C_1$-$C_8$ dialkylamino, Nitro, —COOH, —C(O)—$C_1$-$C_8$ alkyl, —C(O)—$C_6$-$C_{12}$-aryl, $C_1$-$C_8$ alkoxy, $C_1$-$C_8$ haloalkoxy, mercapto, $C_1$-$C_8$ alkylthio, $C_6$-$C_{12}$ arylthio, amido, sulfamido, —$SO_2$—$C_1$-$C_8$ alkyl, $C_1$-$C_8$ alkylamido, $C_1$-$C_8$ dialkylamido, —$SO_2NH$—$C_1$-$C_8$ alkyl, —$SO_2$—$N(C_1$-$C_8$ alkyl$)_2$ and —$SO_3H$, any of which may be optional substituted;

$R_4$ is selected from H, halo, hydroxy, $C_1$-$C_8$ alkyl, $C_1$-$C_8$ haloalkyl, acyl, $C_6$-$C_{12}$ aryl, $C_3$-$C_{12}$ cycloalkyl, $C_7$-$C_{12}$ arylalkyl, $C_3$-$C_{17}$ heteroaryl-alkyl, CN, amino, $C_1$-$C_8$ alkylamino, Nitro, —COOH, —C(O)—$C_1$-$C_8$ alkyl, —C(O)—$C_6$-$C_{12}$-aryl, $C_1$-$C_8$ alkoxy, $C_1$-$C_8$ alkylthio, $C_6$-$C_{12}$ arylthio, amido, sulfamido, —$SO_2$—$C_1$-$C_8$ alkyl, $C_1$-$C_8$ alklamindo, $C_1$-$C_8$ dialklamindo, —$SO_2NH$—$C_1$-$C_8$ alkyl, —$SO_2$—$N(C_1$-$C_8$ alkyl$)_2$ and —$SO_3H$, any of which may be optionally substituted;

A is O, $NR_9$ or S; and $R_9$ is selected from H, $C_1$-$C_8$ alkyl, $C_2$-$C_8$ alkenyl, $C_2$-$C_8$ alkynyl, $C_1$-$C_8$ alkoxy, —OC(O)—$C_1$-$C_8$ alkyl, —OC(O)—$C_6$-$C_{12}$ aryl, $C_3$-$C_{12}$ cycloalkyl, $C_6$-$C_{12}$ aryl, $C_2$-$C_{11}$ heterocyclo alkyl $C_2$-$C_9$ heteroaryl and hydroxy, any of which may be optionally substituted;

optional substituents are selected from alkyl, acyl, alkoxy, alkoxyalkyl, alkoxyalkoxy, alkoxyalkoxy, cyano, halogen, hydroxy, oxo, nitro, haloalkyl, haloalkoxy, amino, alkylamine, dialkylamino, dialkylaminoalkyl, hydroxyalkyl, alkylthio, —$SO_3H$, —$SO_2NH_2$, —$SO_2NH$-alkyl, —$SO_2N$-(alkyl)$_2$, —$CO_2H$, —$CO_2$-alkyl, —$CO_2NH_2$; —$CO_2NH$-alkyl, —$CO_2N$-(alkyl)$_2$, aryl, heteroaryl, aryloxy, and heteroaryloxy;

or a pharmaceutically acceptable salt, thereof.

4. The compound of claim 3, wherein:

$R_1$ is optionally substituted alkenyl;

$R_2$ is aryl, which is substituted;

$R_3$ and $R_5$-$R_8$ are independently selected from H, alkyl, haloalkyl, halo, alkoxy, hydroxy, CN, amino, alkylamino, dialkylamino, alkylthio or —$SO_2NH_2$;

$R_4$ is selected from H, alkyl, haloalkyl, halo, alkoxy, hydroxyl, CN, amino, alkylamino, alkylthio or —$SO_2NH_2$; and A is O;

or a pharmaceutically acceptable salt thereof.

5. The compound of claim 4, wherein:

$R_2$ is aryl, which is substituted; and $R_3$-$R_8$ are independently H, alkyl, haloalkyl, halo, alkoxy, hydroxy, CN and amino;

or a pharmaceutically acceptable salt, thereof.

6. The compound of claim 5, wherein the compound is 1-(4-chlorobenzoyl)-2-vinyl-1,2-dihydroquinoline or a pharmaceutical acceptable salt, thereof.

24

7. A compound of formula (II):

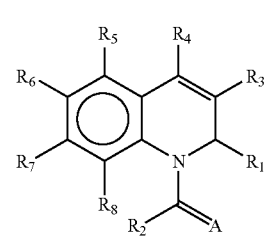

(II)

wherein:

$R_1$ is CN or —C($NR_{10}R_{11}$)=N—$R_{12}$;

$R_2$ is aryl, which is substituted;

$R_3$ and $R_5$-$R_8$ are independently selected from H, halo, hydroxy, alkyl, haloalkyl, acyl, aryl, cycloalkyl, arylalkyl, heteroaryl-alkyl, CN, amino, alkylamino, dialkylamino, nitro, —COOH, —C(O)-alkyl, —C(O)-aryl, alkoxy, haloalkoxy, mercapto, alkylthio, arylthio, amido, sulfamido, sulfonylalkyl, alkylamido, dialkylamido, —$SO_2NH$-alkyl, —$SO_2N$-(alkyl)$_2$ and —$SO_3H$, any of which may be optionally substituted;

$R_4$ is selected from H, halo, hydroxy, alkyl, haloalkyl, acyl, aryl, cycloalkyl, arylalkyl, heteroaryl-alkyl, CN, amino, alkylamino, nitro, —COOH, —C(O)-alkyl, —C(O)-aryl, alkoxy, haloalkoxy, mercapto, alkylthio, arylhthio, amido, sulfamido, sulfonylalkyl, alkylamido, dialkylamido, —$SO_2NH$-alkyl, —$SO_2N$-(alkyl)$_2$ and —$SO_3H$, any of which may be optionally substituted;

A is O, $NR_9$ or S;

$R_{10}$ and $R_{11}$ are independently selected from H, alkyl, aryl, arylalkyl, heteroaryl, heteroaryl-alkyl, cycloalkyl, cycloalkyl-alkyl, heterocycloalkyl and heterocycloalkyl-alkyl, any of which may be optional substituted; and $R_9$ and $R_{12}$ are independently selected from alkoxy, —OC(O)-alkyl, —OC(O)-aryl, cycloalkyl, aryl, heterocycloalkyl, heteroaryl and hydroxy, any of which may be optionally substituted;

or a pharmaceutically acceptable salt thereof;

provided that at least one of $R_3$-$R_8$ is not H or F when A is O and $R_2$ is a phenyl ring, a phenyl ring substituted at the para position with halo, —CN, —$OCH_3$, —$CF_3$ or —$CO_2CH_3$, a quinoline or an ethylene substituted with a phenyl ring or a 3,4-methylenedioxyphenyl moiety;

provided that $R_4$ is not methyl when $R_3$ and $R_5$-$R_8$ are H, A is O and $R_2$ is 4-chlorophenyl; and provided that $R_6$ is not Cl when $R_3$-$R_5$ and $R_7$-$R_8$ are H, $R_1$ is CN and $R_2$ is phenyl.

8. The compound of claim 7, wherein:

$R_2$ is $C_6$-$C_{12}$ aryl, which is substituted;

$R_3$ and $R_5$-$R_8$ are independently selected from the group consisting of H, halo, hydroxyl, $C_1$-$C_8$ alkyl, $C_1$-$C_8$ haloalkyl, acyl, $C_6$-$C_{12}$ aryl, $C_3$-$C_{12}$ cycloalkyl, $C_7$-$C_{12}$ arylalkyl, $C_3$-$C_{17}$ heteroaryl-alkyl, CN, amino, $C_1$-$C_8$ alkylamino, $C_1$-$C_8$ dialkylamino, Nitro, —COOH, —C(O)—$C_1$-$C_8$ alkyl, —C(O)—$C_6$-$C_{12}$-aryl, $C_1$-$C_8$ alkoxy, $C_1$-$C_8$ haloalkoxy, mercapto, $C_1$-$C_8$ alkylthio, $C_6$-$C_{12}$ arylthio, amido, sulfamido, —$SO_2$—$C_1$-$C_8$ alkyl, $C_1$-$C_8$ alkylamido, $C_1$-$C_8$ dialkylamido, —$SO_2NH$—$C_1$-$C_8$ alkyl, —$SO_2$—$N(C_1$-$C_8$ alkyl$)_2$ and —$SO_3H$, any of which may be optional substituted;

$R_4$ is selected from the group consisting of H, halo, hydroxy, $C_1$-$C_8$ alkyl, $C_1$-$C_8$ haloalkyl, acyl, $C_6$-$C_{12}$ aryl, $C_3$-$C_{12}$ cycloalkyl, $C_7$-$C_{12}$ arylalkyl, $C_3$-$C_{17}$ heteroaryl-alkyl, CN, amino, $C_1$-$C_8$ alkylamino, Nitro, —COOH, —C(O)—$C_1$-$C_8$ alkyl, —C(O)—$C_6$-$C_{12}$-aryl, $C_1$-$C_8$ haloalkoxy, mercapto, $C_1$-$C_8$ alkylthio, $C_6$-$C_{12}$ arylthio, amido, sulfamido, —$SO_2$—$C_1$-$C_8$ alkyl, $C_1$-$C_8$ alkylamido, $C_1$-$C_8$ dialkylamido, —$SO_2$NH—$C_1$-$C_8$ alkyl, —$SO_2$—N($C_1$-$C_8$ alkyl)$_2$ and —$SO_3$H, any of which may be optionally substituted;

A is O, $NR_9$ or S; and $R_9$ and $R_{12}$ are independently selected from the group consisting of H, $C_1$-$C_8$ alkyl, $C_2$-$C_8$ alkenyl, $C_2$-$C_8$ alkynyl, $C_1$-$C_8$ alkoxy, —OC(O)—$C_1$-$C_8$ alkyl, —OC(O)—$C_6$-$C_{12}$ aryl, $C_3$-$C_{12}$ cycloalkyl, $C_6$-$C_{12}$ aryl, $C_2$-$C_{11}$ heterocycloalkyl, $C_2$-$C_9$ heteroaryl and hydroxy, any of which may be optionally substituted;

$R_{10}$ and $R_{11}$ are independently selected from the group consisting of H, $C_1$-$C_8$ alkyl, $C_6$-$C_{12}$ aryl, $C_7$-$C_{12}$ arylalkyl, $C_2$-$C_9$ heteroaryl, $C_3$-$C_{17}$ heteroarylalkyl, $C_3$-$C_{12}$ cycloalkyl, $C_4$-$C_{20}$ cycloalkyl-alkyl, $C_2$-$C_{11}$ heterocycloalkyl and $C_3$-$C_{19}$ heterocycloalkyl-alkyl, any of which may be optional substituted;

optional substituents are selected from the group consisting of alkyl, acyl, alkoxy, alkoxyalkyl, alkoxyalkoxy, cyano, halogen, hydroxy, oxo, nitro, haloalkyl, haloalkoxy, amino, alkylamine, dialkylamino, dialkylaminoalkyl, hydroxyalkyl, alkylthio, —$SO_3$H, —$SO_2NH_2$, —$SO_2$NH-alkyl, —$SO_2$N-(alkyl)$_2$, —$CO_2$H, —$CO_2$-alkyl, —$CO_2NH_2$; —$CO_2$NH-alkyl, —$CO_2$N-(alkyl)$_2$, aryl, heteroaryl, aryloxy, and heteroaryloxy;

or a pharmaceutically acceptable salt thereof.

9. The compound of claim 8, wherein:

$R_2$ is aryl, which is substituted;

$R_3$ and $R_5$-$R_8$ are independently selected from H, alkyl, haloalkyl, halo, alkoxy, hydroxy, CN, amino, alkylamino, dialkylamino, alkylthio or —$SO_2NH_2$;

$R_4$ is selected from H, alkyl, haloalkyl, halo, alkoxy, hydroxyl, CN amino, alkylamino, alkylthio or —$SO_2NH_2$;

A is O;

$R_9$ and $R_{12}$ are independently selected from the group consisting of H, alkyl, and hydroxy; and $R_{10}$ and $R_{11}$ are independently H or alkyl;

or a pharmaceutically acceptable salt thereof.

10. The compound of claim 9, wherein:

$R_2$ is aryl, which is an optionally substituted phenyl;

$R_3$-$R_8$ are independently H, alkyl, haloalkyl, halo, alkoxy, hydroxy, CN and amino;

$R_9$ and $R_{12}$ are independently H or hydroxy; and $R_{10}$ and $R_{11}$ are H;

or a pharmaceutically acceptable salt thereof.

11. The compound of claim 10, wherein the compound is selected from the group consisting of:

1-(4-chlorobenzoyl)-6-methyl-1,2-dihydroquinoline-2-carbonitrile;

1-(4-chlorobenzoyl)-N'-hydroxy-6-methyl-1,2-dihydroquinoline-2-carboximidamide;

4,7-dichloro-1-(4-fluorobenzoyl)-1,2-dihydro-quinoline-2-carbonitrile;

1-(4-chlorobenzoyl)-6-nitro-1,2-dihydroquinoline-2-carbonitrile;

6-chloro-1-(4-chlorobenzoyl)-1,2-dihydroquinoline-2-carbonitrile;

1-(4-chlorobenzoyl)-7-methyl-1,2-dihydroquinoline-2-carbonitrile;

5-chloro-1-(4-chlorobenzoyl)-1,2-dihydroquinoline-2-carbonitrile; or 4,7-dichloro-1-benzoyl-1,2-dihydroquinoline-2-carbonitrile;

and or a pharmaceutically acceptable salt thereof.

12. The compound of claim 10, wherein the compound is 1-(4-chlorobenzoyl)-6-methyl-1,2-dihydroquinoline-2-carbonitrile or a pharmaceutically acceptable salt thereof.

* * * * *

UNITED STATES PATENT AND TRADEMARK OFFICE
CERTIFICATE OF CORRECTION

PATENT NO.       : 7,553,967 B2
APPLICATION NO.  : 11/076936
DATED            : June 30, 2009
INVENTOR(S)      : Matthew Olson et al.

It is certified that error appears in the above-identified patent and that said Letters Patent is hereby corrected as shown below:

ON THE TITLE PAGE ITEM (56) COL. 1 REFERENCES CITED:

OTHER PUBLICATIONS, "Acta Crystallographic" should read --Acta Crystallographica--.

COLUMN 2:

Line 67, "optional" should read --optionally--.

COLUMN 3:

Line 15, "phenyl." should read --phenyl;--.

COLUMN 4:

Line 17, "optional" should read --optionally--.

COLUMN 5:

Line 15, "sisting" should read --sisting of--; and
Line 67, "sisting" should read --sisting of--.

COLUMN 6:

Line 50, "sisting" should read --sisting of--.

COLUMN 8:

Line 13, "denote" should read --denotes--.

COLUMN 9:

Line 8, "—$SO_2$NHalkyl," should read -- —$SO_2$NH alkyl,--;
Line 9, "$CO_2$NHalkyl," should read --$CO_2$NH alkyl,--;
Line 32, "—$SO_2$NH alkyl—C—$C_8$ alkyl," should read
    -- —$SO_2$NH alkyl—$C_1$—$C_8$ alkyl,--;
Line 34, "optional" should read --optionally--;
Line 65, "—$SO_2$NH—$C_{1-8}$" should read -- —$SO_2$NH—$C_1$—$C_8$--; and
Line 67, "optional" should read --optionally--.

UNITED STATES PATENT AND TRADEMARK OFFICE
CERTIFICATE OF CORRECTION

PATENT NO. : 7,553,967 B2
APPLICATION NO. : 11/076936
DATED : June 30, 2009
INVENTOR(S) : Matthew Olson et al.

It is certified that error appears in the above-identified patent and that said Letters Patent is hereby corrected as shown below:

COLUMN 10:

Line 5, "alkyl $C_2$-$C_9$ heteroaryl" should read --alkyl, $C_2$-$C_9$ heteroaryl--;
Line 12, "optional" should read --optionally--;
Line 46, "optional" should read --optionally--;
Line 51, "alkyl $C_2$-$C_9$ heteroaryl" should read --alkyl, $C_2$-$C_9$ heteroaryl--; and
Line 58, "optional" should read --optionally--.

COLUMN 16:

Line 12, "polyrA-oligodTi2-18" should read --polyrA-oligodT$_{12-18}$--;
Line 18, "polyrA-oligodT12-18" should read --polyrA-oligodT$_{12-18}$--; and
Line 58, "polyrA oligodT$_{12-18}$" should read --polyrA-oligodT$_{12-18}$--.

COLUMN 22:

Line 41, "heteroaryl" should read --heteroaryl,--;
Line 56, "—C(O)-alkyl," should read -- —C(O)-aryl,--; and
Line 64, "and" should be deleted.

COLUMN 23:

Line 16, "optional" should read --optionally--;
Line 23, "$C_1$-$C_8$ alkoxy, $C_1$-$C_8$ alkylthio," should read --$C_1$-$C_8$ alkoxy, $C_1$-$C_8$ haloalkoxy, mercapto, $C_1$-$C_8$ alkylthio,--; and
Line 34, "alkyl $C_2$-$C_9$" should read --alkyl, $C_2$-$C_9$--.

COLUMN 24:

Line 26, "optional" should read --optionally--; and
Line 65, "optional" should read --optionally--.

COLUMN 25:

Line 4, "aryl, $C_1$-$C_8$ haloalkoxy," should read --aryl, $C_1$-$C_8$ alkoxy, $C_1$-$C_8$ haloalkoxy,--;
Line 22, "optional" should read --optionally--; and
Line 29, "—$CO_2HN_2$;" should read -- —$CO_2HN_2$,--.

UNITED STATES PATENT AND TRADEMARK OFFICE
CERTIFICATE OF CORRECTION

PATENT NO. : 7,553,967 B2
APPLICATION NO. : 11/076936
DATED : June 30, 2009
INVENTOR(S) : Matthew Olson et al.

It is certified that error appears in the above-identified patent and that said Letters Patent is hereby corrected as shown below:

<u>COLUMN 26</u>:

Line 2, "hydroxyl, CN amino," should read --hydroxy, CN, amino,--.

Signed and Sealed this

Twenty-ninth Day of December, 2009

David J. Kappos
*Director of the United States Patent and Trademark Office*